(12) United States Patent
Tkaczyk et al.

(10) Patent No.: US 9,243,888 B2
(45) Date of Patent: Jan. 26, 2016

(54) IMAGE MAPPED OPTICAL COHERENCE TOMOGRAPHY

(75) Inventors: Tomasz S. Tkaczyk, Houston, TX (US); Mark Pierce, Piscataway, NJ (US)

(73) Assignee: William Marsh Rice University, Houston, TX (US)

( * ) Notice: Subject to any disclaimer, the term of this patent is extended or adjusted under 35 U.S.C. 154(b) by 112 days.

(21) Appl. No.: 13/991,657

(22) PCT Filed: Nov. 30, 2011

(86) PCT No.: PCT/US2011/062503
§ 371 (c)(1),
(2), (4) Date: Jun. 5, 2013

(87) PCT Pub. No.: WO2012/078417
PCT Pub. Date: Jun. 14, 2012

(65) Prior Publication Data
US 2013/0250290 A1    Sep. 26, 2013

Related U.S. Application Data

(60) Provisional application No. 61/422,053, filed on Dec. 10, 2010.

(51) Int. Cl.
*G01N 21/00* (2006.01)
*G01B 9/02* (2006.01)
(Continued)

(52) U.S. Cl.
CPC .......... *G01B 9/02091* (2013.01); *A61B 5/0066* (2013.01); *A61B 5/6852* (2013.01); *G01J 3/021* (2013.01); *G01J 3/2823* (2013.01); *G01J 3/453* (2013.01)

(58) Field of Classification Search
CPC ... H01J 37/32935; G01N 21/64; G01N 21/68; G01N 2015/1037; G01J 3/02
USPC ..................... 356/300–334, 72–73
See application file for complete search history.

(56) References Cited

U.S. PATENT DOCUMENTS 8,045,177 B2    10/2011    Tearney et al.
8,174,694 B2 *   5/2012    Bodkin .................. 356/328
(Continued)

FOREIGN PATENT DOCUMENTS

WO    2010/053979 A2    5/2010

OTHER PUBLICATIONS

Gao et al.; "compact imaging slicing spectrometer (ISS) for hyperspectral fluorescence microscope"; Optics Express, vol. 17, No. 15, Jul. 6, 2009, pp. 12293-12308.*
(Continued)

*Primary Examiner* — Abdullahi Nur
(74) *Attorney, Agent, or Firm* — Osha Liang LLP

(57) ABSTRACT

A method for imaging a sample. The method includes, during a single acquisition event, receiving depth-encoded electromagnetic (EM) fields from points on a sample that includes a first depth-encoded EM field for a first point and a second depth-encoded EM field for a second point, and redirecting the first depth-encoded EM field along a first predetermined direction to a first location on a dispersing re-imager and the second depthencoded EM field along a second pre-determined direction to a second location on the dispersing re-imager. The method further includes spectrally dispersing the first depthencoded EM field to obtain a first spectrum, re-imaging the first spectrum onto a first location on a detector, spectrally dispersing the second depth-encoded EM field to obtain a second spectrum, re-imaging the second spectrum onto a second location on the detector, and detecting the first re-imaged spectrum and the second re-imaged spectrum.

12 Claims, 10 Drawing Sheets

(51) Int. Cl.
  *A61B 5/00* (2006.01)
  *G01J 3/02* (2006.01)
  *G01J 3/28* (2006.01)
  *G01J 3/453* (2006.01)

(56) References Cited

U.S. PATENT DOCUMENTS

| | | | |
|---|---|---|---|
| 2003/0025913 A1 | 2/2003 | Izatt et al. | |
| 2005/0171438 A1 | 8/2005 | Chen et al. | |
| 2008/0088852 A1 | 4/2008 | Rogers et al. | |
| 2008/0262314 A1* | 10/2008 | Tearney et al. | 600/160 |

OTHER PUBLICATIONS

Sabatke et al.; " Snapshot imaging spectropolarimeter" ; Optical Engineering, vol. 41, No. 5, Jan. 1, 2002, pp. 1048-1054.*

International Search Report issued in PCT/US2011/062503 mailed on Feb. 14, 2012 (3 pages).

Written Opinion of the International Searching Authority issued in PCT/US2011/062503 mailed on Feb. 14, 2012 (7 pages).

Li, P. et al.; "Spectral-Domain Optical Coherence Tomography and Applications for Biological Imaging"; Biophotonics, Nanophotonics and Metamaterials, 2006. Metamaterials 2006. International Symposium On, IEEE, PI, Oct. 1, 2006, pp. 222-225 (4 pages).

Fercher, A. F. et al.; "Optical coherence tomography—principles and applications", Reports On Progress In Physics, Institute of Physics Publishing, Bristol, GB, vol. 66, Jan. 20, 2003, pp. 239-303 (65 pages).

International Report on Patentability issued in PCT/US2011/062503 mailed Jun. 20, 2013 (7 pages).

Office Action in related U.S. Appl. No. 13/992,101 mailed Dec. 18, 2014 (19 pages).

Gao et al : "Compact Image Sizing Spectrometer (ISS) for hyperspectral fluorescence microscopy"; Optics Express, vol. 17, No. 15, Jul. 20, 2009, pp. 12293-12308 (16 pages).

Sabatke, D. et al., "Snapshot imaging spectropolarim"; Optical Engineering, vol. 41. No. 5, Jan. 1, 2002, pp. 1048-1054 (7 pages).

* cited by examiner

IMAGE MAPPED OPTICAL COHERENCE TOMOGRAPHY

CROSS REFERENCE TO RELATED APPLICATIONS

This application claims priority under 35 U.S.C. §119(e) to U.S. Provisional Patent Application Ser. No. 61/422,053, which is incorporated by reference in its entirety.

STATEMENT REGARDING FEDERALLY SPONSORED RESEARCH OR DEVELOPMENT

This invention was made with government support under Grant Number EB011598 awarded by the National Institutes of Health. The government has certain rights in the invention.

BACKGROUND

Optical coherence tomography (OCT) systems are essential tools for diagnostic imaging of all kinds. For example, OCT systems have been used to image biological samples. Traditional OCT systems require multiple passes of the sample in order to generate the image.

SUMMARY

In general, in one aspect, the invention relates to a method for imaging a sample. The method includes, during a single acquisition event, receiving a plurality of depth-encoded electromagnetic (EM) fields from a plurality of points on a sample that includes a first depth-encoded EM field for a first point and a second depth-encoded EM field for a second point, and redirecting the first depth-encoded EM field along a first pre-determined direction to a first location on a dispersing re-imager and the second depth-encoded EM field along a second pre-determined direction to a second location on the dispersing re-imager. The method further includes spectrally dispersing the first depth-encoded EM field to obtain a first spectrum, re-imaging the first spectrum onto a first location on a detector, spectrally dispersing the second depth-encoded EM field to obtain a second spectrum, re-imaging the second spectrum onto a second location on the detector, and detecting the first re-imaged spectrum and the second re-imaged spectrum.

In general, in one aspect, the invention relates to a system that includes and image mapper, dispersing re-imager, and a detector. The image mapper is configured to, during a single acquisition event, receive a plurality of depth-encoded electromagnetic (EM) fields from a plurality of points on a sample comprising a first depth-encoded EM field for a first point and a second depth-encoded EM field for a second point, and redirect the first depth-encoded EM field along a first pre-determined direction to a first location on a dispersing re-imager and the second depth-encoded EM field along a second pre-determined direction to a second location on the dispersing re-imager. The dispersing re-imager is configured to spectrally disperse the first depth-encoded EM field to obtain a first spectrum, re-image the first spectrum on to a first location on a detector, spectrally disperse the second depth-encoded EM field to obtain a second spectrum, and re-image the second spectrum on to a second location on the detector. The detector is configured to detect the first re-imaged spectrum and the second re-imaged spectrum.

Other aspects of the invention will be apparent from the following description and the appended claims.

DETAILED DESCRIPTION

Figure 1:
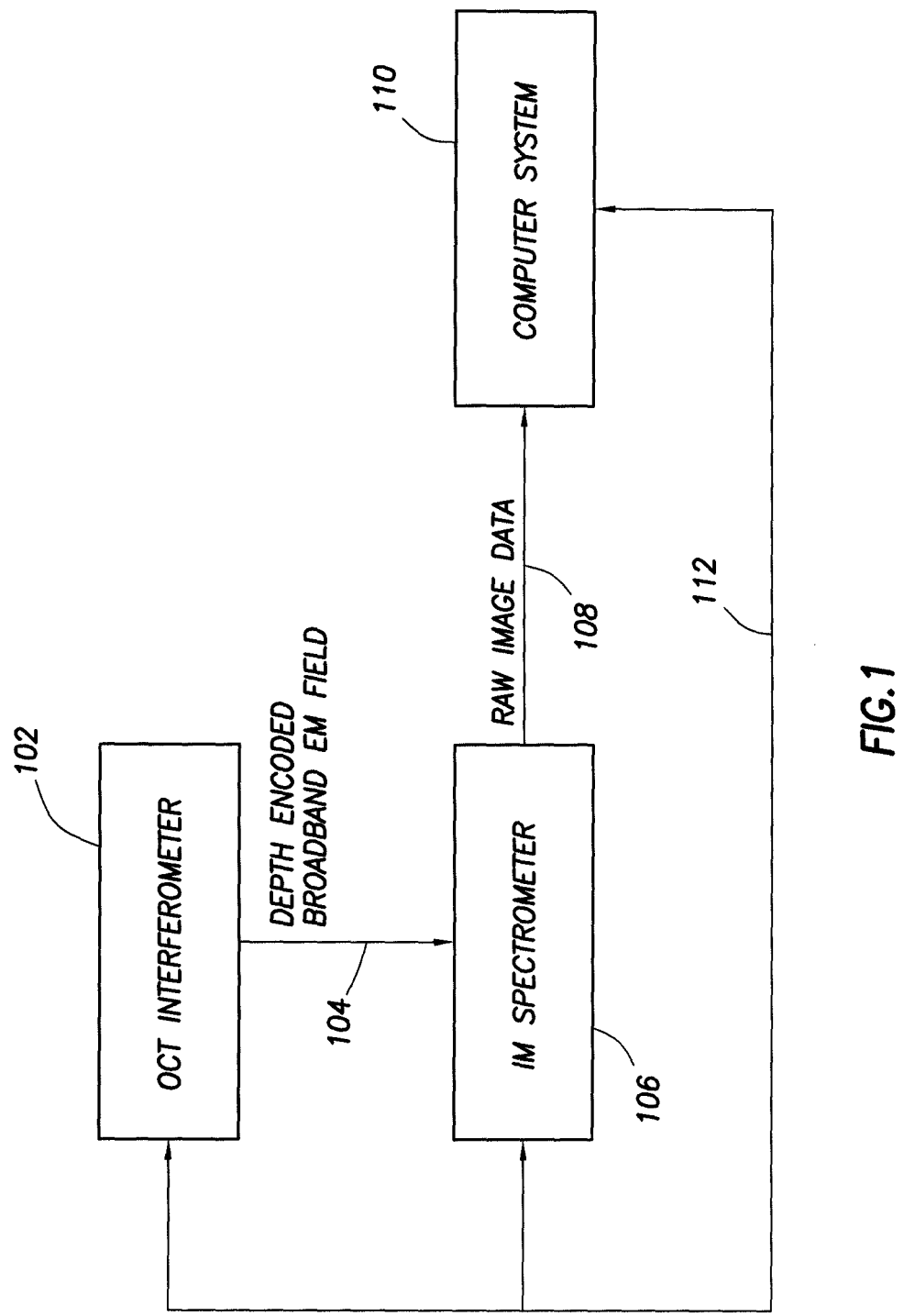
FIG. 1 shows a system in accordance with one or more embodiments of the invention.

Specific embodiments of the invention will now be described in detail with reference to the accompanying figures. Like elements in the various figures are denoted by like reference numerals for consistency. Further, the use of "Fig." in the drawings is equivalent to the use of the term "Figure" in the description.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

In general, embodiments of the invention relate to image mapped optical coherence tomography. More specifically, embodiments of the invention relate to spectral domain optical coherence tomography (SD-OCT) employing an image mapping spectrometer. One or more embodiments of the invention relate to a system and method for producing a three-dimensional (3D) image of a sample in a single snapshot or single acquisition event.

For purposes of this invention, a sample is any biological or non-biological material, object, or specimen, which may be imaged. In one embodiment of the invention, a sample includes a number of sample points. A sample point may reside at a particular (x,y,z) location in the sample. Sample points may further serve as source points for backscattered electromagnetic (EM) radiation.

In one embodiment of the invention, a single acquisition event may occur when a detector simultaneously detects a number of EM fields emanating from multiple points on the surface (in the x,y plane) of a sample being illuminated. The EM fields emanating from each of the multiple points may correspond to EM fields emanating from various positions along the z-direction for the point located at the x,y position in the x,y plane. In one embodiment of the invention, emanating refers to EM waves that are reflected, scattered, backscattered, or otherwise emitted from a location on the sample. In one embodiment of the invention, the acquisition event begins and ends when the detector begins to detect EM radiation and finishes detecting the EM radiation, respectively.

EM radiation, EM waves, and EM fields are assumed to be synonymous and may be used interchangeably within the following detailed description. A broadband EM field may be defined as an EM field that includes many different wavelengths or frequencies. It will be understood that the term optical coherence tomography may not be used to limit the spectral domain of the present invention to merely optical wavelengths or frequencies as the technique may also be used outside the visible EM spectrum.

In one embodiment of the invention, a depth-encoded EM field may originate from a sample point where information relating to the sample depth profile along the direction of propagation of the EM field at the sample point is encoded within the broadband spectrum of the EM field.

FIG. 1 shows a system in accordance with one or more embodiments of the invention. The system includes SD-OCT interferometer 102 that may output depth-encoded broadband EM field 104. Depth-encoded broadband EM field 104 has encoded within its frequency spectrum depth information regarding a sample being imaged. Image mapping spectrometer 106 is configured to receive depth-encoded broadband EM field 104. Image mapping spectrometer 106 is configured to convert the depth-encoded broadband EM field 104 into a raw image data cube 108. Raw image data cube 108 may be in the form of a 3D dataset (x, y, D(x, y, λ)) where D(x, y, λ) is the value of a spectral interferogram obtained at every (x,y) sample point that is located within a field of view of the optical system used to image the sample. Computer system 110 is configured to receive data including raw image data cube 108. In one embodiment of the invention, the computer 110 includes a processor, memory, one or more output devices (e.g., a display, a printer, etc.), one or more input devices (e.g., a keyboard, a mouse, etc.), and software stored in the memory, which when executed by the processor, is configured to process the raw image data cube 108.

Computer system 110 may be further configured to process a plurality of spectral interferograms D(x, y, λ) and to extract a backscattered intensity along the depth (z-direction) of the sample. Thus, computer system 110 may convert the 3D dataset to a 3D image of the sample, which may be then output to a display. One of ordinary skill will understand that several different methods may be used to convert spectral information into depth information according to known methods of SD-OCT. For example, the data in each spectral interferogram D(x, y, λ) may be numerically remapped to D(x, y, k) and then Fourier transformed. Furthermore, the data processing may include standard image mapping spectrometer remapping, and/or include mapping from image sensor pixel directly to wavenumber k. The processing may also implement the standard techniques for compensating dispersion in the system. In addition, one of ordinary skill will understand that data processing may be accomplished via hardware that may be integrated into image mapping spectrometer 106.

Further, user feedback 112 may be received at computer system 110 for performing various actions on one or both of the image mapping spectrometer 106 and SD-OCT interferometer 102. For example, the sample may be moved to allow the viewing of a region of interest (ROI) to the user or the user may wish to zoom into or out of the sample ROI. Zoom may be accomplished spatially and/or spectrally.

Figure 2:
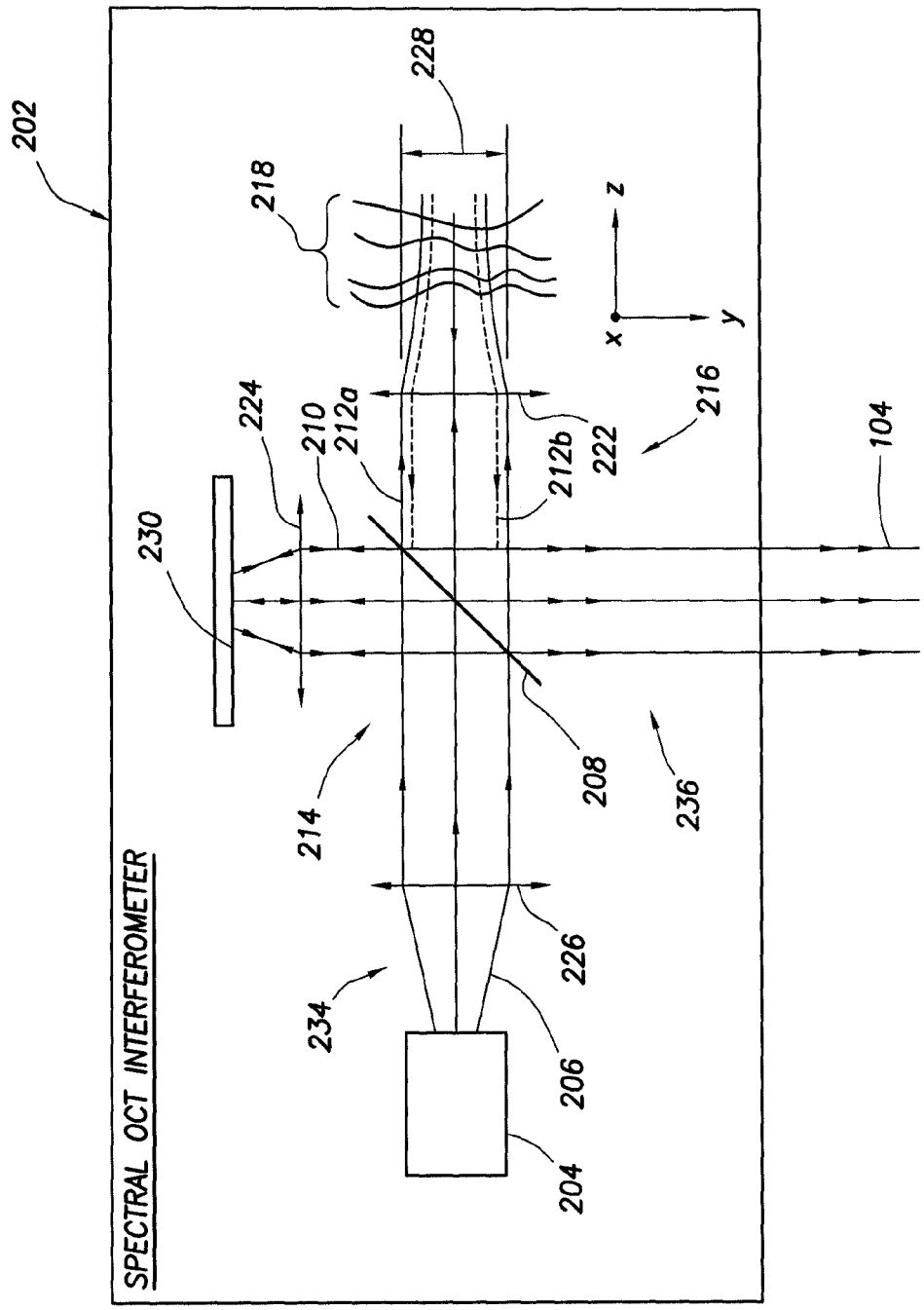
FIG. 2 shows a schematic view of a Spectral Domain OCT Interferometer in accordance with one or more embodiments of the invention.

FIG. 2 shows a schematic view of a SD-OCT interferometer configured to produce a depth-encoded broadband EM field in accordance with one or more embodiments of the invention. SD-OCT interferometer 202 may include input arm 234, reference arm 214, sample arm 216, and output arm 236. Input arm 234 includes a source 204 of broadband EM radiation configured to output source beam 206. According to one embodiment of the invention, source 204 may be a superluminescent diode (SLD) or any other suitable broadband source known in the art, for example, amplified spontaneous emission (ASE) fiber sources, superfluorescence sources, photonic crystal fiber sources, thermal sources, etc. Source beam 206 may be collimated as necessary with output collimator 226.

Beamsplitter 208 is configured to split source beam 206 into two beams: reference beam 210 that propagates through reference arm 214 and sample beam 212a that propagates through sample arm 216. Reference arm 214 further includes reference objective 224 and mirror 230. Reference beam 210 is configured to pass through reference objective 224, reflect off of mirror 230, and propagate back through reference objective 224 along a path that substantially overlaps with incoming reference beam 210. Sample arm 216 further includes sample objective 222 and sample 218. Furthermore, in an exemplary embodiment, the sample arm may include a coherent fiber optic bundle (not shown) to transmit light to/from a remote sample location, for example a site inside the body. Sample objective 222 may be configured to illuminate a spatially extended portion of the sample 218. In one exemplary embodiment, the sample beam 212a at the sample 218 may illuminate a volume including the entire field of view 228 of sample objective 222. Backscattered portion 212b of sample beam 212a (shown offset from sample beam 212a in the sample arm 216, for clarity) is configured to propagate back through sample objective 222 along a path that substantially overlaps with sample beam 212a. Beamsplitter 208 is further configured to recombine reference beam 210 and backscattered portion 212b of sample beam 212a resulting in an interference of reference beam 210 with backscattered portion 212b to create depth-encoded broadband EM field 104. Depth-encoded broadband EM field 104 includes 2D spatial information, related to the (x,y) reflectivity of the sample, encoded across the spatial extent of the depth-encoded broadband EM field 104. The depth-encoded broadband EM field 104 further includes 1D spatial or depth information encoded within its frequency spectrum. The spatial or depth information is related to the reflectivity along a depth direction z of the sample for every (x,y) point illuminated by sample beam 212a.

One of ordinary skill will understand that any known interferometer geometry may be used without departing from the scope of the invention. For example, a Linnik or wide field Linnik interferometer configuration may be used, or a common path interferometer employing a single Mirau objective may be used. In addition, in an exemplary embodiment, reference objective 224 may be identical in design to a sample objective 222.

Figure 3:
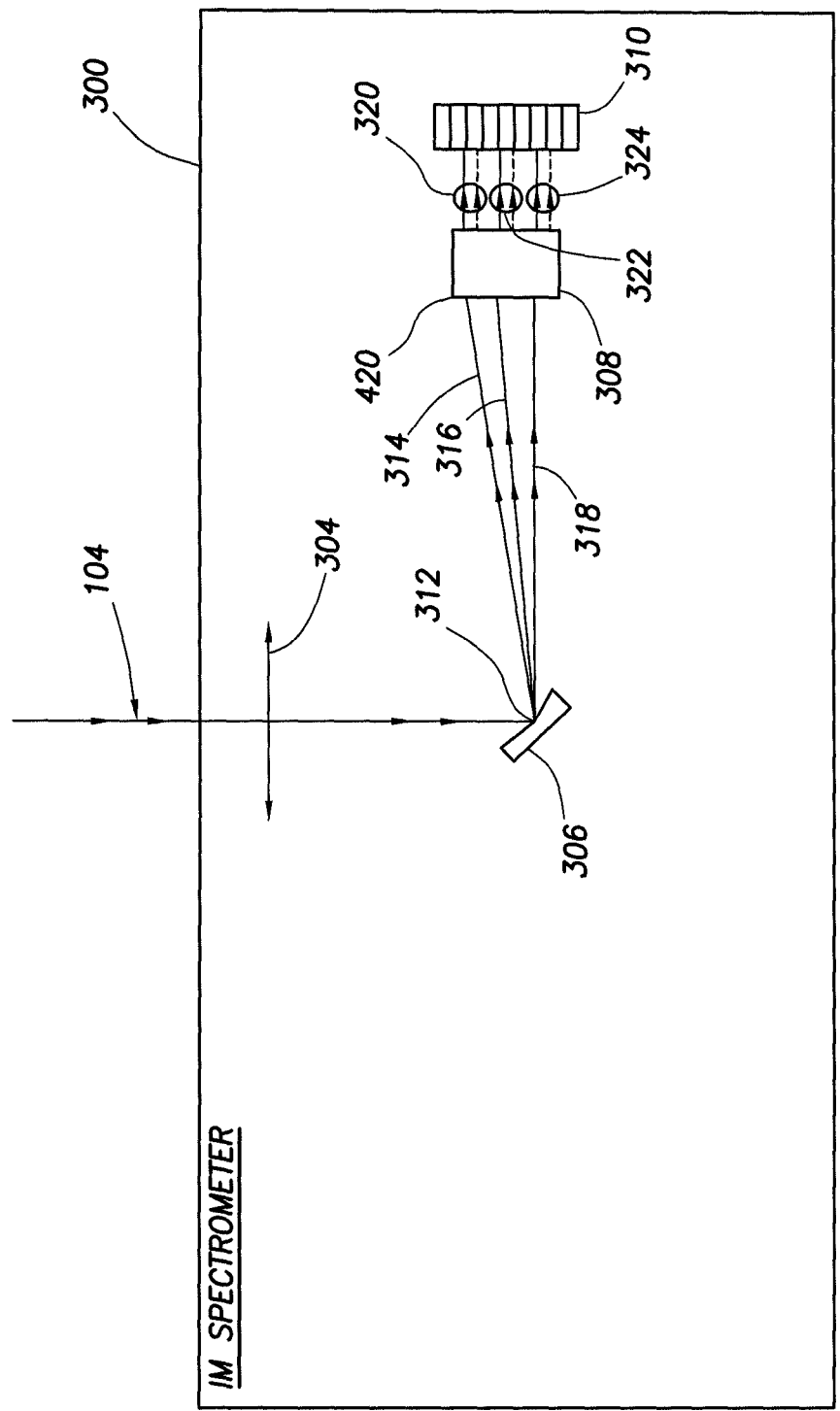
FIG. 3 shows a schematic view of an image mapping spectrometer in accordance with one or more embodiments of the invention.

FIG. 3 shows a schematic view of an image mapping spectrometer in accordance with one or more embodiments of the invention. Image mapping spectrometer 300 includes focusing lens 304, image mapper 306, dispersing reimager 308, and detector array 310. Image mapping spectrometer 300 is configured to receive depth-encoded broadband EM field 104 originating from SD-OCT interferometer 202 and to map, spectrally disperse, and reimage depth-encoded broadband EM field 104 onto detector 310.

Focusing lens 304 is configured to focus depth-encoded broadband EM field 104 at image mapper 306, thus, forming an image 312 of sample 218 at the image mapper 306. Image mapper 306 is configured to redirect, or map, a plurality of portions of the image 312 to a plurality of locations on the front surface 420 of dispersing reimager 308. For clarity, only 3 mapped image portions, 314, 316, and 318, represented by single rays are represented in FIG. 3. Dispersing reimager 308 is configured to collect and spectrally disperse mapped image portions 314, 316, and 318 thus creating spectra 320, 322, 324. For clarity, FIG. 3 shows the spectral dispersion that would result if each of image portions 314, 316, and 318 included only two distinct wavelengths. Furthermore, dispersing reimager 308 is configured to reimage spectra 320, 322, and 324 onto detector 310. Detector 310 may include a 2D array of EM radiation detectors, for example in the form of a charged coupled device (CCD) chip or and array of CCD chips.

Figure 4A:
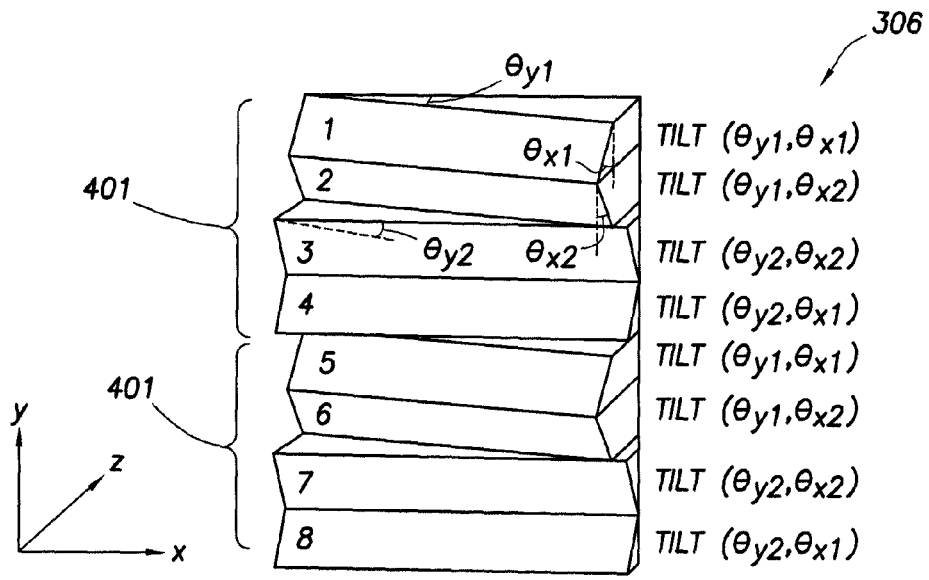
FIG. 4A shows a schematic view of an image mapper in accordance with one or more embodiments of the invention.

FIG. 4A shows a schematic view of an image mapper in accordance with one or more embodiments of the invention. The image mapper 306 includes eight elongated reflective surfaces 1-8. Each reflective surface 1-8 is oriented according to rotation angles $(\theta_y, \theta_x)$ about the y and x axes, respectively. Thus, each reflective surface 1-8 may redirect, or map, a portion of image 312 to a location on the front surface 420 of dispersing reimager 308, as shown in FIG. 3. Image mapper 306 shown in FIG. 4A includes four distinct angles for the eight reflective surfaces arranged in two repeating groups 401.

Figure 4B:
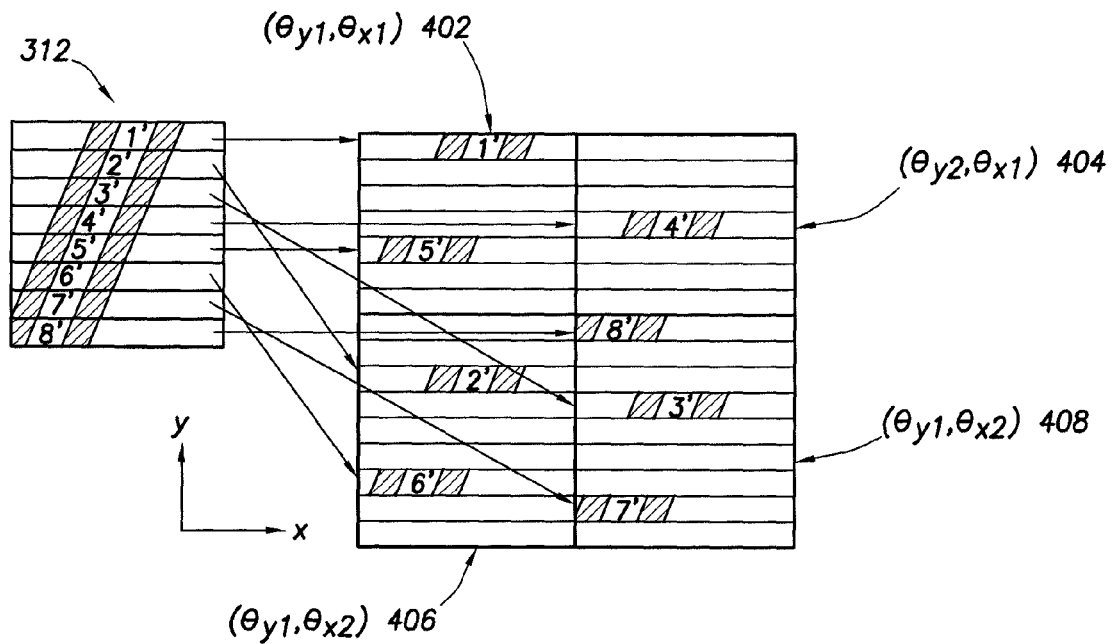
FIG. 4B shows a schematic view of the front surface of a dispersing reimager in accordance with one or more embodiments of the invention.

FIG. 4B shows a schematic view of the front surface 420 of dispersing reimager 308 in accordance with one or more embodiments of the invention. Front surface 420 may be divided into four regions 402, 404, 406, and 408. Each region receives a portion 1'-8' of image 312 that has originated from a reflective surface having one of the four distinct angles. Region 402 corresponds to image portions 1' and 5', which originate from reflective surface 1 and 5, respectively, each having the same tilt of $(\theta_{y1}, \theta_{x1})$. Region 404 corresponds to image portions 4' and 8', which originate from reflective surface 4 and 8, respectively, each having the same tilt of $(\theta_{y2}, \theta_{x1})$. Region 406 corresponds to portions image 2' and 6', which originate from reflective surface 2 and 6, respectively, each having the same tilt of $(\theta_{y1}, \theta_{x2})$. Region 408 corresponds to image portions 3' and 7', which originate from reflective surface 3 and 7, respectively, each having the same tilt of $(\theta_{y2}, \theta_{x2})$.

One of ordinary skill in the art will understand that image mapper 306 may be fabricated with any number of reflective surfaces having any number of angles or sizes and may be grouped or ungrouped according to angle. In general, example M x-angles and N y-angles result in M×N distinct image mapper surfaces that map to M×N distinct regions on front surface 420 of dispersing reimager 308. However, by using M x-angles and N y-angles that are grouped in L repeating groups, a system having M×N×L distinct image mapper surfaces that map to only M×N distinct regions on front surface 420 of dispersing reimager 308 is possible. For example, according to the embodiment shown in FIGS. 4A-4B, M=2, N=2 and L=2. Thus, eight distinct image mapper surfaces are available for image mapping but only four distinct regions (each region receiving a pair of mapped portions of the image 312) on front surface 420 of dispersing reimager 308 are needed for reimaging onto the detector. This may result in smaller, less complicated reimaging optics and smaller, less complicated detectors when compared to image mappers that do not employ angle grouping.

One of ordinary skill in the art will understand that the image mapper may be a refractive or diffractive optical element rather than a reflective optical element without departing from the scope of the disclosure. Furthermore, any optical element known in the art that can induce a suitable angular deflection in the path of a beam of EM radiation may be used. For example, prisms may be used induce the deflection or optical fibers or any other suitable waveguide may be used to redirect the image to the dispersing reimager.

Furthermore, an image mapper may include dynamic components to allow for dynamic operations, for example optical zoom. For example, dynamic microelectromechanical system ("MEMS") mirror arrays may be used in place of the static mirror surfaces disclosed above. In addition, liquid crystal modulators or micro fluidic based refractive liquid modulators may be employed.

Furthermore, one of ordinary skill in the art will recognize that a telescope or beam expander (not shown) may be optionally inserted into image mapping spectrometer 106, for example, in front of focusing lens 304 in order to preserve the image resolution by matching the size of the image point spread function (the diffraction limited spot size) with the width of a single reflective surface 1-8 of the image mapper 306. In another embodiment of the invention, the beam expander may be configured to be telecentric in both image and object space.

Figure 5:
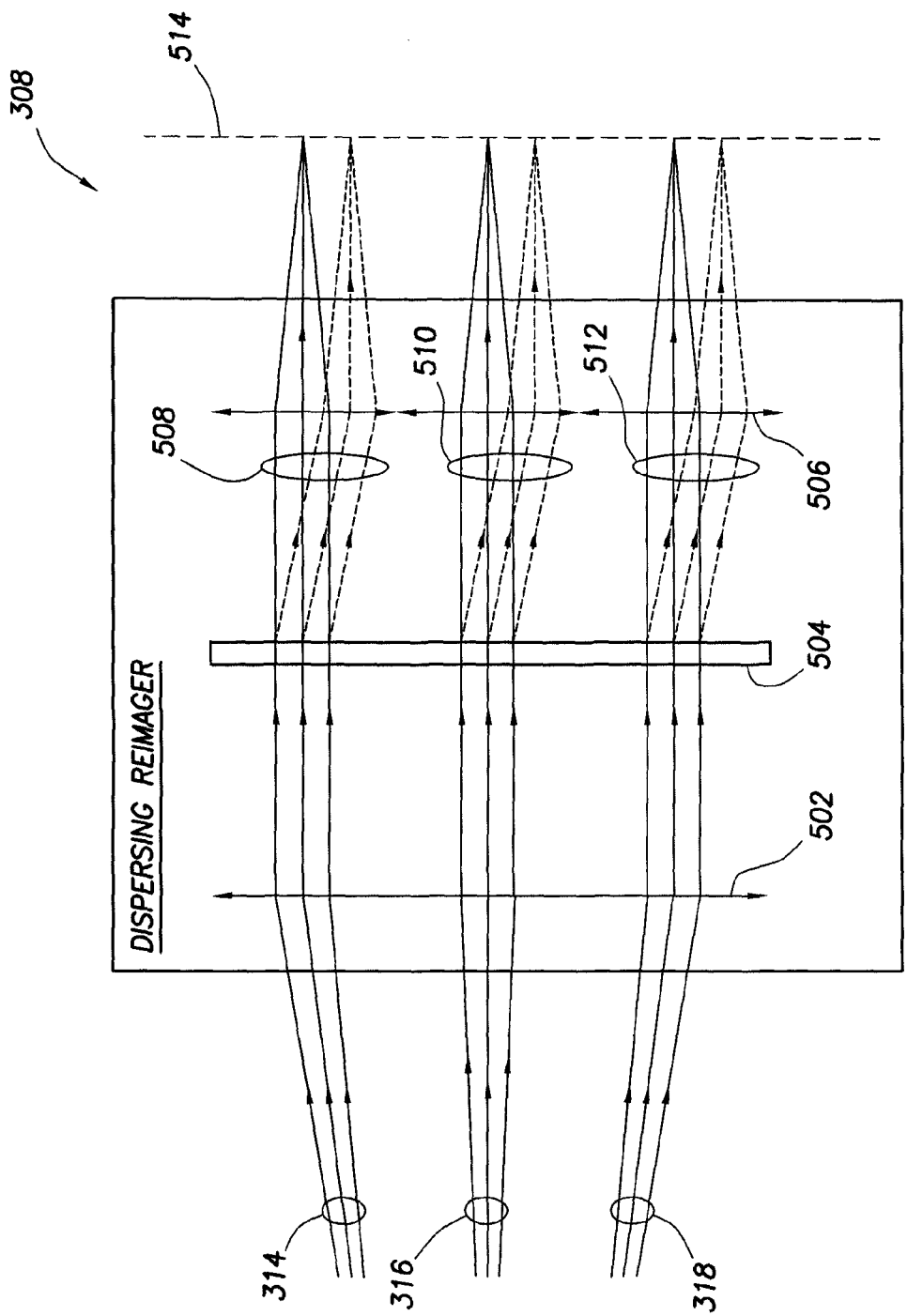
FIG. 5 shows a schematic view of a dispersing reimager in accordance with one or more embodiments of the invention.

FIG. 5 shows a schematic view of a dispersing reimager in accordance with one or more embodiments of the invention. For clarity, only three mapped image portions, 314, 316, and 318, represented by groups of three rays each are depicted. Dispersing reimager 308 includes collecting lens 502, dispersive element 504, and reimaging lens array 506. Collecting lens 502 is configured to collimate mapped image portions 314, 316, and 318. Dispersive element 504 is configured to spectrally disperse the collimated mapped image portions 314, 316, and 318. Dispersive element 504 may include any optical element known in the art having dispersive characteristics, for example, a single prism or diffraction grating. Furthermore, dispersive element 504 may include of an array of prisms or diffraction gratings. For clarity, only two sets of dispersed rays are shown in FIG. 5 as would be the case for mapped image portions including only two spectral components. As shown in FIG. 5, the dispersive element 504 is configured to spatially separate the spectral components of collimated mapped image portions 314, 316, and 318 to form image mapped spectra 508, 510, and 512. Reimaging lens array 506 is configured to reimage image mapped spectra 508, 510, and 512 onto detector plane 514.

One of ordinary skill in the art will recognize that a telescope or beam expander (not shown) may be optionally inserted into dispersing reimager 308, for example, between collecting lens 502 and dispersive element 504 in order to adjust the spatial extent of collimated mapped image portions 314, 316, and 318 in order to match the spatial extent of the reimaging lens array 506, as necessary. Furthermore, one of ordinary skill in the art will recognize that dispersive element 504 may include dynamic or tunable dispersers that enable optical zooming of spectral (and, thus, depth) ROIs. Furthermore, one of ordinary skill in the art will recognize that the individual elements of the dispersive imager 308 may be reordered, without departing from the scope of the invention as disclosed herein. For example, reimaging lens array 506 may come before dispersive element 504.

Figure 6:
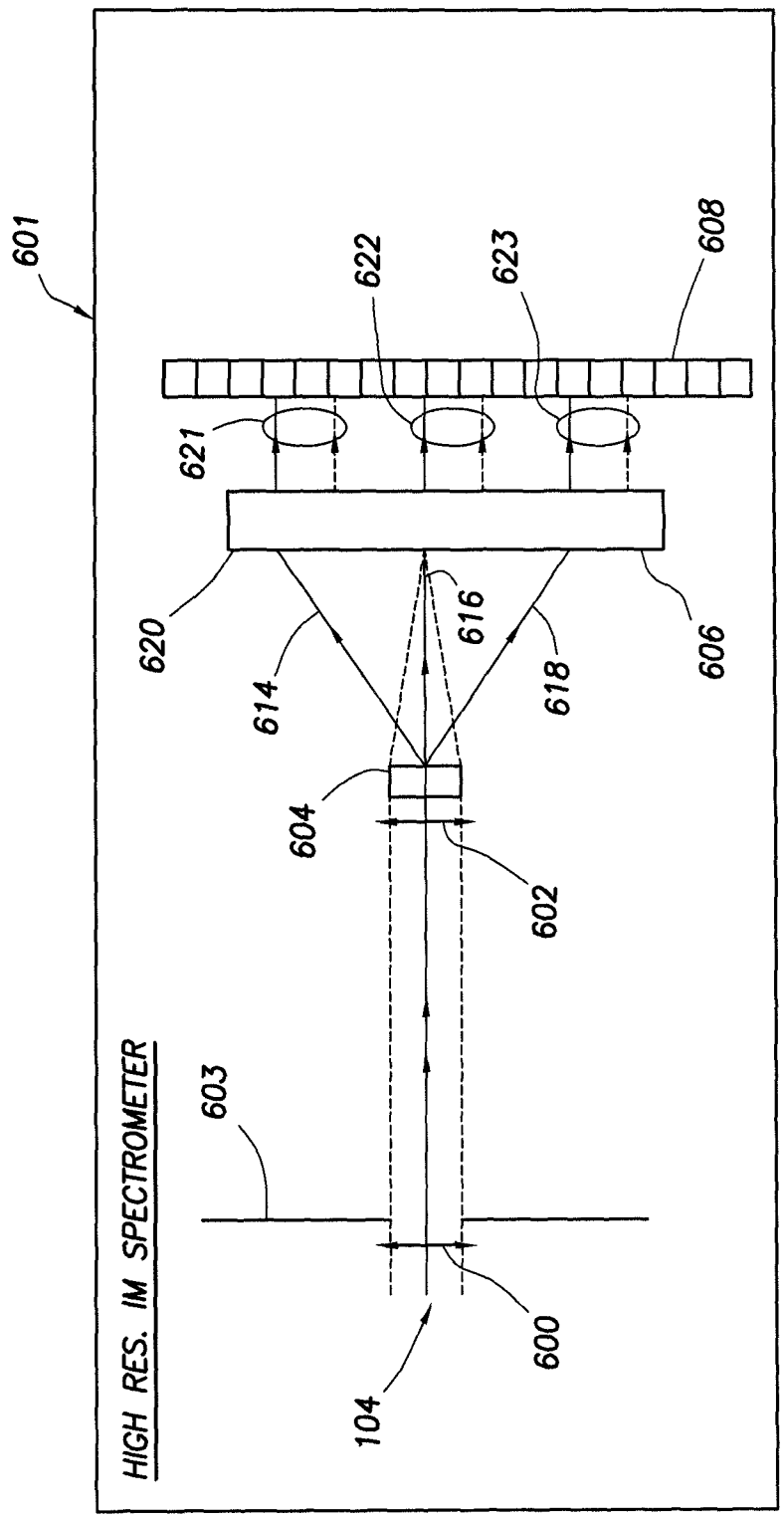
FIG. 6 shows a schematic view of a compact high resolution image mapping spectrometer in accordance with one or more embodiments of the invention.

FIG. 6 shows a schematic view of a compact high resolution image mapping spectrometer in accordance with one or more embodiments of the invention. The compact, high resolution image mapping spectrometer 601 may operate in the place of image mapping spectrometer 106 as part of the system for image mapped optical coherence tomography as shown in FIG. 1. The compact high resolution image mapping spectrometer 601 includes focusing lens 600, field lens 602, refractive image mapper 604, dispersing reimager 606, and detector 608. Furthermore, detector 608 may include a 2D array of photo-detectors, for example in the form of a CCD chip or and array of CCD chips.

Focusing lens 600 is configured to focus depth-encoded broadband EM field 104 at refractive image mapper 604, forming an image 612 of sample 218 at the refractive image mapper 604. Field lens 602 is configured to preserve high optical throughput and compactness of the spectrometer 601 by re-imaging the exit pupil 603 of focusing lens 600 onto dispersing reimager 606. Refractive image mapper 604 is configured to redirect, or map, a plurality of portions of image 612 to a plurality of locations on the front surface 620 of dispersing reimager 606. For clarity, only three mapped image portions, 614, 616, and 618, represented by single rays are represented in FIG. 6. Field lens 602 is located in close proximity to refractive image mapper 604, thus, facilitating the redirection of mapped image portions 614, 616, 618 to the dispersing reimager 606 over a relatively short distance without the need for a bulky large diameter collecting lens (e.g., collecting lens 502 shown in FIG. 5). Dispersing reimager 606 is configured to collect and spectrally disperse mapped image portions 614, 616, and 618 thus creating spectra 621, 622, 632. For clarity, FIG. 6 shows the spectral dispersion that would result if each of image portions 614, 616, and 618 included only two distinct wavelengths. Furthermore, dispersing reimager 606 is configured to reimage spectra 621, 622, 632 onto detector 608.

In accordance with one or more embodiments of the invention, refractive image mapper 604 may include an array of prisms. Furthermore, refractive image mapper 604 may be manufactured using methods such as diamond raster fly cutting from a machineable optical material such as zinc sulfide. Furthermore, refractive image mapper 604 may be manufactured by ruling, injection molding, glass press molding, hot embossing, or any other method known in the art.

Figure 7:
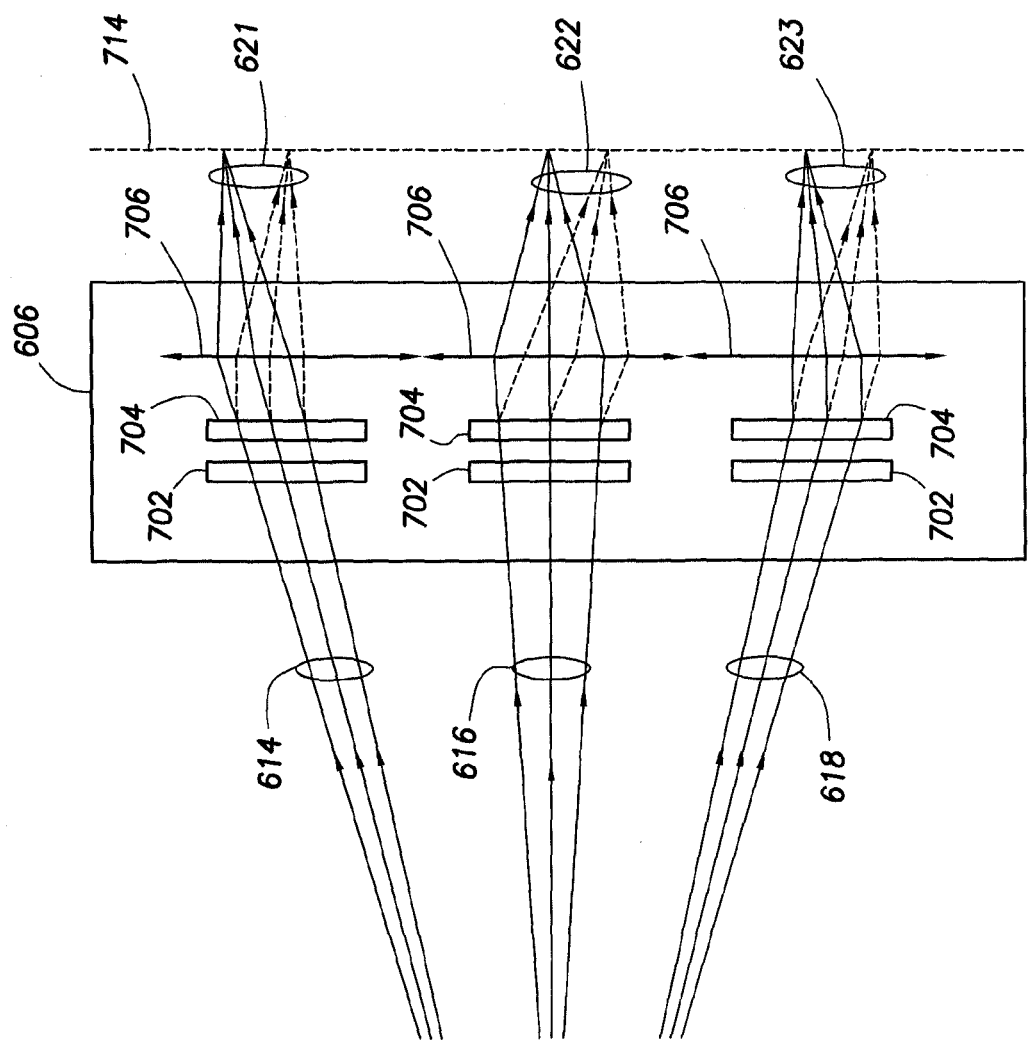
FIG. 7 shows a schematic view of a dispersing reimager in accordance with one or more embodiments of the invention to be employed in a compact, high resolution image mapping spectrometer.

FIG. 7 shows a schematic view of a dispersing reimager 606 in accordance with one or more embodiments of the invention to be employed in a compact, high resolution image mapping spectrometer 601. For clarity, only three mapped image portions, 614, 616, and 618, are depicted. Dispersing reimager 606 includes an array of field of view correctors 702, an array of dispersive elements 704, and an array of reimaging lenses 706. Field of view correctors 702 are configured to laterally shift the fields of view of each of reimaging lens 706 to ensure that the dispersing reimager 606 is within the field of view of each reimaging lens 706. Dispersive elements 704 are configured to spectrally disperse the mapped image portions 614, 616, and 618. Dispersive element 704 may include any optical element known in the art having dispersive characteristics, for example, a single prism, a prism pair or a diffraction grating. For clarity, only two sets of dispersed rays are shown in FIG. 7 as would be the case for mapped image portions including only two spectral components. As shown in FIG. 7, the dispersive elements 704 are configured to spatially separate the spectral components of mapped image portions 614, 616, and 618 to form image mapped spectra 708, 710, and 712. Reimaging lenses 706 are configured to reimage image mapped spectra 708, 710, and 712 onto detector plane 714.

Furthermore, one of ordinary skill in the art will recognize that the individual elements of the dispersive imager 606 may be reordered, without departing from the scope of the invention as disclosed herein. For example, reimaging lens array 706 may come before dispersive element 704.

Figure 8:
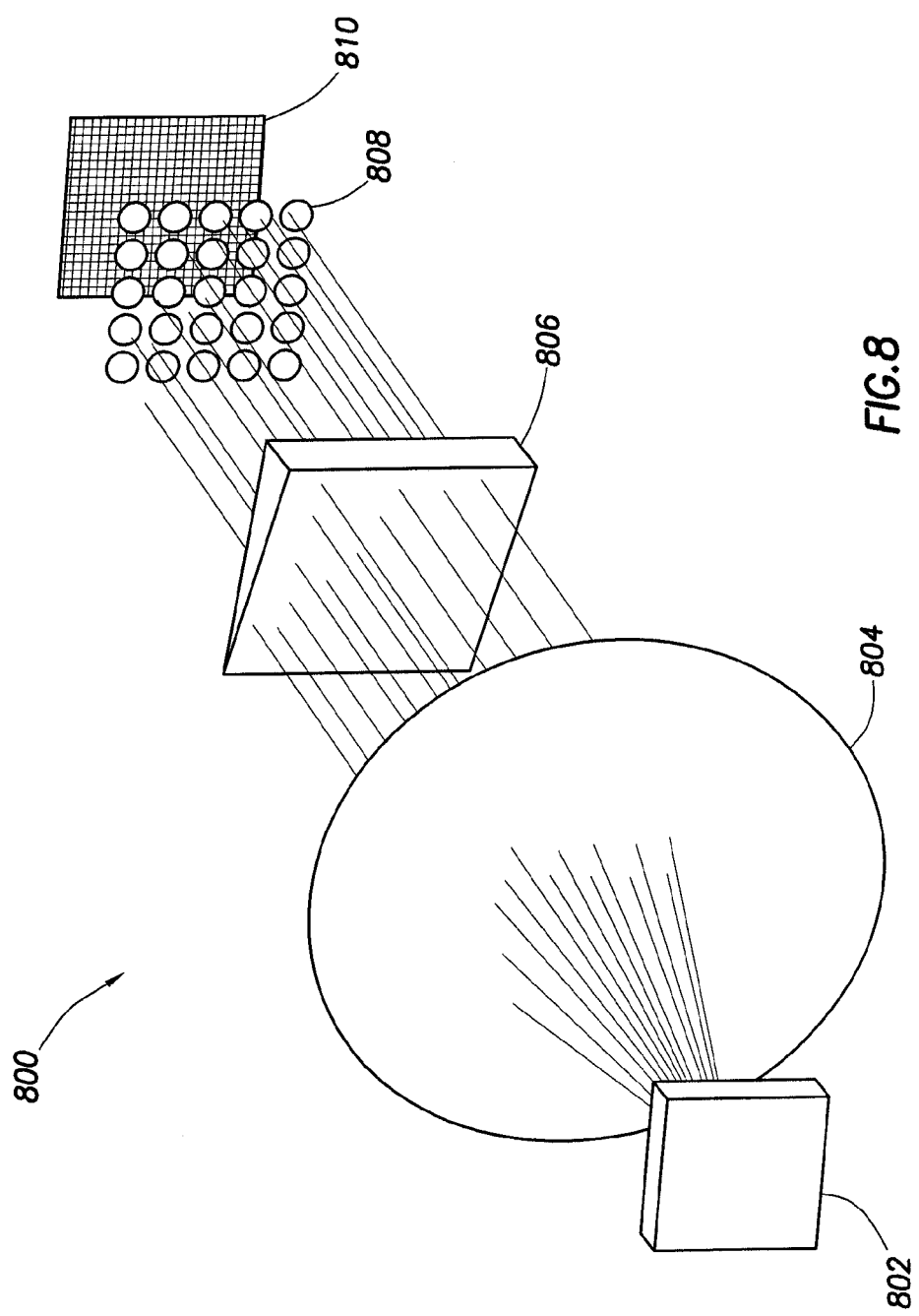
FIG. 8 shows a perspective view of a portion of an image mapping spectrometer in accordance with one or more embodiments of the invention.

FIG. 8 shows a perspective view of a portion of an image mapping spectrometer in accordance with one or more embodiments of the invention. Image mapping spectrometer 800 includes image mapper 802, collecting lens 804, dispersive element 806, and reimaging lens array 808. Collecting lens 804 is configured to collimate a plurality of portions of a mapped image, similarly to that shown in FIG. 5. The plurality of portions of the mapped image are shown as a plurality of rays, for clarity. Dispersive element 806 is configured to spectrally disperse (not shown) the plurality collimated mapped image portions, similarly to that shown in FIG. 5. Dispersive element 806 may include any optical element known in the art having dispersive characteristics, for example, a single prism, prism pair, or diffraction grating. Furthermore, dispersive element 806 may include an array of prisms or an array diffraction gratings. Reimaging lens array 808 is configured to reimage image the plurality of mapped spectra onto detector array 810.

As shown in FIG. 8, reimaging lens array 808 includes a five by five array of reimaging lenses. Thus, this system may be employed with, for example, an image mapper 802 having 25 distinct mirror or refractor surfaces each with a distinct angle or, for example, may be employed with an image mapper 802 having 100 distinct mirror or refractor surfaces grouped in four groups having 25 mirror or refractor surfaces with distinct angles each.

Figure 9:
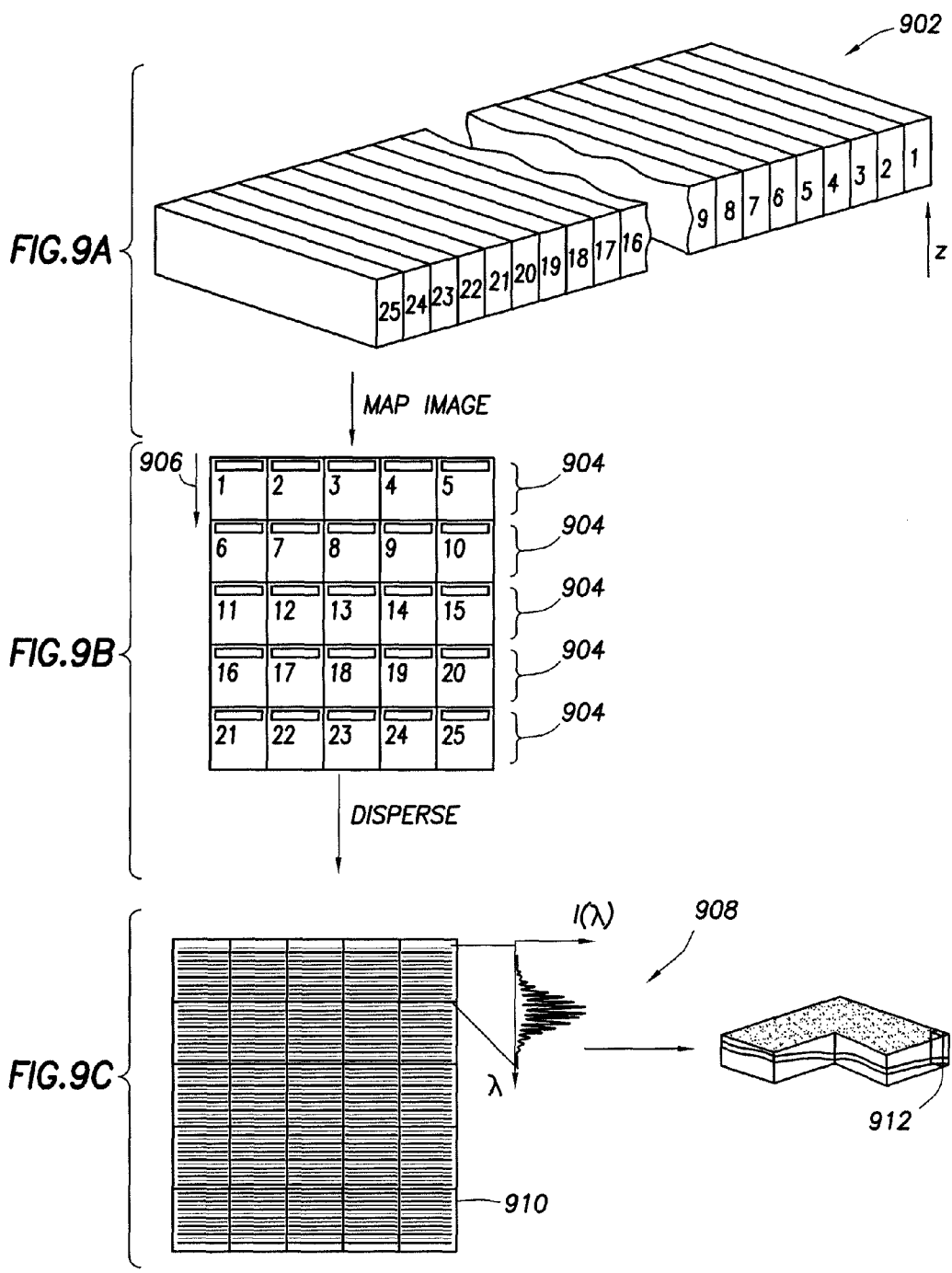
FIGS. 9A-C shows a graphical flow chart that illustrates the operational principles of image mapped optical coherence tomography.

FIGS. 9A-C further an example of image mapped optical coherence tomography according to one or more embodiments of the invention. FIG. 9A depicts sample 902 that may include, for example, various biological tissues, a metallurgical sample, a thin film, or any other sample wherein it is desired to acquire a 3D image in a single acquisition event. An intermediate image of sample 902 may be image mapped in accordance with the description above with reference to FIGS. 1-8. In this embodiment, an image mapper is employed that includes 25 distinct reflective surfaces configured to produce a mapped image that includes 25 distinct image slices 1-25.

One effect of the image mapping is to redirect or map these 25 slices to 25 different sub-locations 1-25 on the front surface of, for example, a dispersing reimager as described in FIGS. 4, 5, and 7. An example of 25 distinct slices of an image located at 25 different sub-locations on the front surface of a dispersing reimager is shown in FIG. 9B. Alternatively, a number L of grouped elements may be employed in the image mapper as described in reference to FIGS. 4A-4B which will result in L image slices being present at each sub-location.

It is useful to note that FIG. 9B may alternatively be interpreted to depict the refocused image on the detector array if the dispersive elements were not present in the dispersing reimager. In this scenario, multiple image slices 1-25 would be separated on the detector by 25 non-illuminated or dark regions 904. The dark regions that separate the 25 image slices allow room for each slice to be spectrally dispersed by spatial separation of the spectral components of each point that makes up an image slice. Spatial separation of the spectral components occurs according to the description above in reference to FIGS. 2-8 along spectral separation directions 906.

Thus, the result of image mapping, followed by spectral dispersion and reimaging onto a detector array 910, is a plurality of spectral interferograms 908, an example of which is shown in FIG. 9C according to one or more embodiments of the invention. Thus, each sub-detector (or pixels in the case of a CCD) on the detector array measures the value of a spectral interferogram D(x, y, λ) that originates from a specific point (x,y) on the sample. One of ordinary skill will understand that several different methods may be used to convert spectral information into depth information according to known methods of SD-OCT, for example by numerically remapping D(x, y, λ) to D(x, y, k) and taking a Fourier transform of D(x, y, k). Thus, one column of the detector array contains the information for one complete depth scan 912 through the image. Accordingly, one single acquisition event of the detector array is enough to acquire all the information necessary for a full 3D reconstruction of the sample that is within the field of view of the imaging system used to illuminate the sample.

Figure 10:
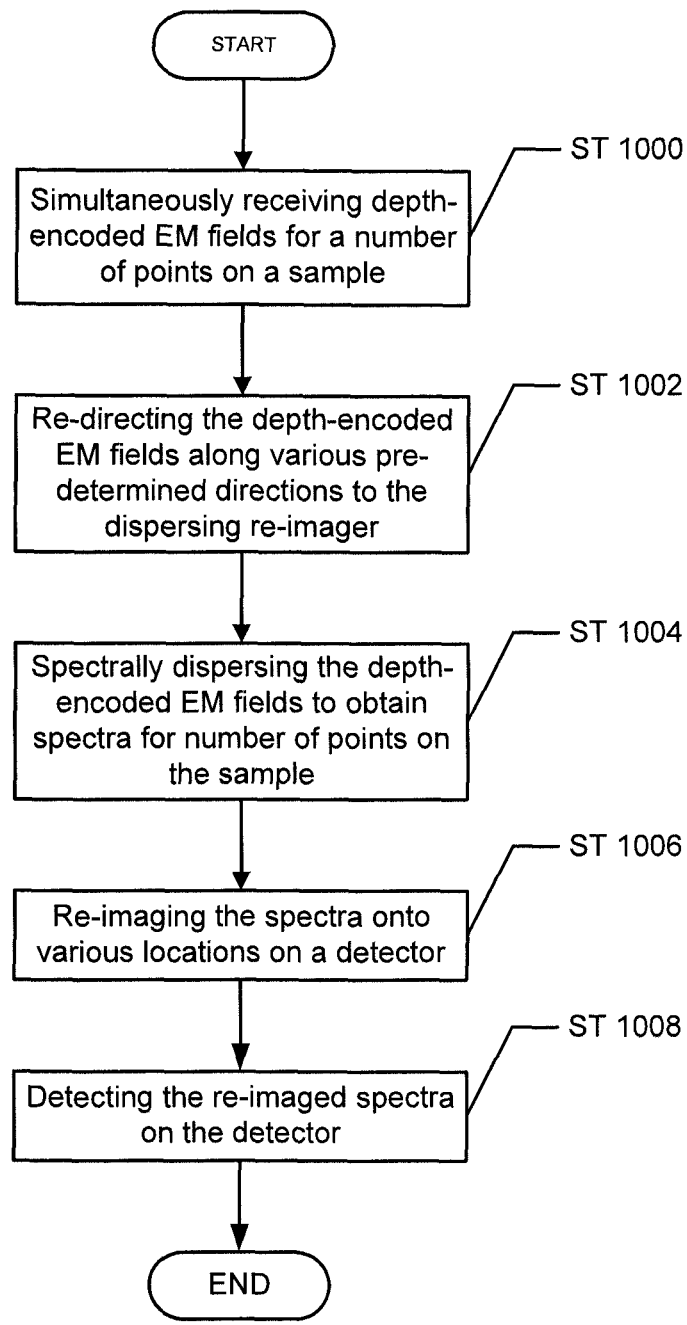
FIG. 10 shows a flow chart describing a method in accordance with one or more embodiments of the invention.

FIG. 10 shows a flow chart describing a method in accordance with one or more embodiments of the invention. While the various steps in the flowchart are presented and described sequentially, one of ordinary skill will appreciate that some or all of the steps may be executed in different orders, may be combined, or omitted, and some or all of the steps may be executed in parallel.

In Step 1000, simultaneously receiving depth-encoded EM fields for a number of points on a sample during a single acquisition event. In Step 1002, re-directing the depth-encoded EM fields along various pre-determined directions to the dispersing re-imager. In one embodiment of the invention, Step 1002 is performed by the image mapper. In Step 1004, the depth-encoded EM fields are spectrally dispersed to generate spectra, where the spectra includes one spectrum for each of the number of points referenced in Step 1000. In Step 1006, re-imaging the spectra to various location on a detector. In Step 1008, detecting the re-imaged spectra on the detector. At this stage, a computer (or other processing device) uses the re-imaged spectra to generate a 3D image of the sample.

One or more embodiments of the invention may provide an image mapped SD-OCT system that may acquire a full 3D image of a sample in a single acquisition event of the detector or detector array without the need for scanning of the source beam position or tuning of the source beam wavelength. One or more embodiments of the invention may allow for a rugged, spatially compact system without moving parts, thus reducing cost and increasing the utility in applications requiring small areas, such as endoscopy. One or more embodiments of the invention allow for high speed acquisition of full 3D images, thus reducing artifacts caused by sample motion. One or more embodiments of the invention allow for an increased signal-to-noise ratio over existing SD-OCT systems by increasing the fraction of time during 3D image acquisition that is devoted to light collection and by increasing optical throughput through the system.

One of ordinary skill will appreciate that image mapped optical coherence tomography may be employed with any known from OCT and is not limited simply to SD-OCT. For example, one or more embodiments may employ Doppler OCT or polarization sensitive OCT without departing from the scope of the present disclosure.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for imaging a sample, comprising:
during a single acquisition event:
receiving a plurality of depth-encoded electromagnetic (EM) fields from a plurality of points on a sample comprising a first depth-encoded EM field for a first point and a second depth-encoded EM field for a second point;
redirecting the first depth-encoded EM field along a first pre-determined direction to a first location on a dispersing re-imager and the second depth-encoded EM field along a second pre-determined direction to a second location on the dispersing re-imager;
spectrally dispersing the first depth-encoded EM field to obtain a first spectrum;
re-imaging the first spectrum onto a first location on a detector;
spectrally dispersing the second depth-encoded EM field to obtain a second spectrum;
re-imaging the second spectrum onto a second location on the detector; and
detecting the first re-imaged spectrum and the second re-imaged spectrum.

2. The method of claim 1, wherein the first depth-encoded EM field comprises a plurality of EM fields emanating along a z-direction in the sample for the first point.

3. A system, comprising:
an image mapper configured to, during a single acquisition event:
receive a plurality of depth-encoded electromagnetic (EM) fields from a plurality of points on a sample comprising a first depth-encoded EM field for a first point and a second depth-encoded EM field for a second point; and
redirect the first depth-encoded EM field along a first pre-determined direction to a first location on a dispersing re-imager and the second depth-encoded EM field along a second pre-determined direction to a second location on the dispersing re-imager;
the dispersing re-imager configured to:
spectrally disperse the first depth-encoded EM field to obtain a first spectrum;
re-image the first spectrum on to a first location on a detector;
spectrally disperse the second depth-encoded EM field to obtain a second spectrum; and
re-image the second spectrum on to a second location on the detector; and
the detector configured to:
detect the first re-imaged spectrum and the second re-imaged spectrum.

4. The system of claim 3, further comprising:
a spectral domain optical coherence tomography (SD-OCT) system configured to generate the plurality of depth-encoded EM fields and provide the plurality of depth-encoded EM fields to the image mapper.

5. The system of claim 4, further comprising:
a field lens interposed between the SD-OCT and the image mapper and configured to receive the plurality of depth-encoded EM fields from the SD-OCT.

6. The system of claim 3, wherein the first depth-encoded EM field comprises a plurality of EM fields emanating along a z-direction in the sample for the first point.

7. The system of claim 3, wherein the image mapper is refractive.

8. The system of claim 7, wherein the dispersing re-imager comprises an array of field of view correctors configured to receive the plurality of depth-encoded EM fields from the image remapper and to shift each of the plurality of depth-encoded EM fields to obtained a plurality of shifted depth-encoded EM fields.

9. The system of claim 8, wherein the dispersing re-imager further comprises an array of dispersive elements configured to receive the plurality of shifted depth-encoded EM fields and to spectrally disperse each of the plurality of spectra comprising the first spectrum and the second spectrum.

10. The system of claim 9, wherein the dispersing re-imager further comprises an array of reimaging lenses configured to the plurality of spectra and to re-image the plurality of spectra on to the detector.

11. The system of claim 3, wherein the detector comprises a two-dimensional (2D) array of EM radiation detectors.

12. The system of claim 11, the detector is a charged-couple device.

* * * * *